United States Patent
Pauser et al.

(10) Patent No.: US 7,806,297 B2
(45) Date of Patent: Oct. 5, 2010

(54) DEVICE FOR STORING, MIXING AND DISPENSING A FREE-FLOWING MATERIAL

(75) Inventors: Helmut Pauser, Diessen (DE); Marc Peuker, Schondorf (DE); Arno Hohmann, München (DE)

(73) Assignee: 3M Innovative Properties Company, St. Paul, MN (US)

( * ) Notice: Subject to any disclaimer, the term of this patent is extended or adjusted under 35 U.S.C. 154(b) by 1836 days.

(21) Appl. No.: 10/495,324

(22) PCT Filed: Nov. 18, 2002

(86) PCT No.: PCT/EP02/12899

§ 371 (c)(1), (2), (4) Date: May 11, 2004

(87) PCT Pub. No.: WO03/041605

PCT Pub. Date: May 22, 2003

(65) Prior Publication Data

US 2004/0262332 A1  Dec. 30, 2004
US 2008/0099507 A9  May 1, 2008

(30) Foreign Application Priority Data

Nov. 16, 2001 (DE) ............................... 101 56 075

(51) Int. Cl.
*A61C 5/06* (2006.01)
*B05C 17/01* (2006.01)
*B01F 13/00* (2006.01)

(52) U.S. Cl. .................. 222/129; 222/145.6; 222/459

(58) Field of Classification Search ............. 222/145.6, 222/459, 129; 366/337–339; 604/82
See application file for complete search history.

(56) References Cited

U.S. PATENT DOCUMENTS

| 2,869,543 | A | * | 1/1959 | Ratcliff et al. ................. 604/90 |
| 3,635,444 | A | | 1/1972 | Potter |
| 3,923,288 | A | | 12/1975 | King |
| 4,674,661 | A | | 6/1987 | Herold |
| 4,693,706 | A | * | 9/1987 | Ennis, III ...................... 604/87 |
| 4,808,184 | A | | 2/1989 | Tepic |
| 4,811,549 | A | * | 3/1989 | Usami et al. ............. 222/145.6 |
| 4,941,751 | A | * | 7/1990 | Muhlbauer ............... 366/182.1 |
| 4,989,758 | A | | 2/1991 | Keller |
| 5,487,606 | A | | 1/1996 | Keller |
| 5,498,078 | A | | 3/1996 | Keller |
| 5,819,988 | A | | 10/1998 | Sawhney et al. |
| 6,065,645 | A | | 5/2000 | Sawhney et al. |
| 6,165,632 | A | | 12/2000 | Blum et al. |

(Continued)

FOREIGN PATENT DOCUMENTS

DE    92 09 105.9    12/1993

(Continued)

*Primary Examiner*—Kenneth Bomberg

(57) ABSTRACT

The invention relates to a device comprising a mixer tube (2), whose diameter diminishes toward one end, a mixer helix (5), which is located inside the mixer tube (2), and comprising a plunger (6,7). According to the invention, the mixer helix can or should be accordingly compressed inside the mixer tube with the aid of the plunger that is inserted into the mixer tube. The device enables a largely complete dispensing of the material remaining in a static mixer helix during mixing and is suited, above all, for storing, mixing and dispensing dental materials.

28 Claims, 4 Drawing Sheets

U.S. PATENT DOCUMENTS

| | | | |
|---|---|---|---|
| 6,234,795 B1 | 5/2001 | Fischer | |
| 6,309,372 B1 * | 10/2001 | Fischer et al. | 604/82 |
| 6,884,071 B2 * | 4/2005 | Martin | 222/145.6 |
| 2004/0033466 A1 | 2/2004 | Shellard et al. | |
| 2008/0195082 A1 * | 8/2008 | Pauser et al. | 604/85 |

FOREIGN PATENT DOCUMENTS

| | | |
|---|---|---|
| DE | 100 22 160 A1 | 11/2001 |
| EP | 0 157 121 A1 | 10/1985 |
| EP | 0 261 466 A1 | 3/1988 |
| EP | 0 157 121 B1 | 11/1988 |
| EP | 0 261 466 B1 | 7/1990 |
| EP | 0 407 805 A1 | 1/1991 |
| EP | 0 584 428 A1 | 3/1994 |
| EP | 0 664 153 A1 | 7/1995 |
| EP | 0 584 428 B1 | 3/1996 |
| EP | 0 664 153 B1 | 3/1999 |
| EP | 1 389 448 A1 | 2/2004 |
| WO | WO 86/06618 A1 | 11/1986 |
| WO | WO 00/21842 A2 | 4/2000 |

* cited by examiner

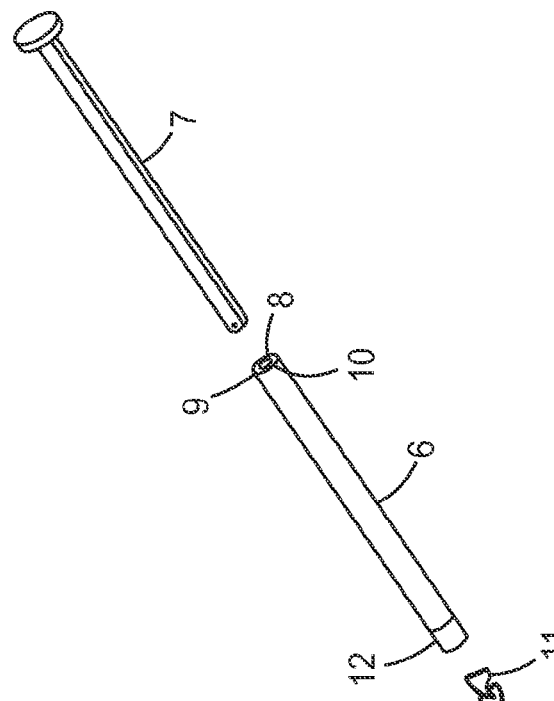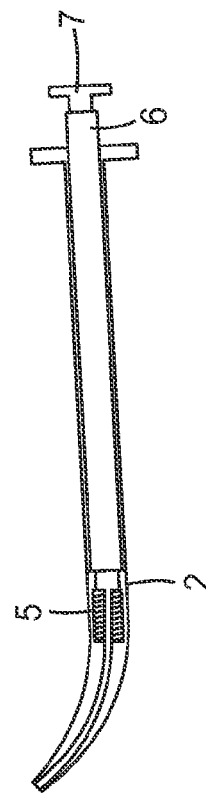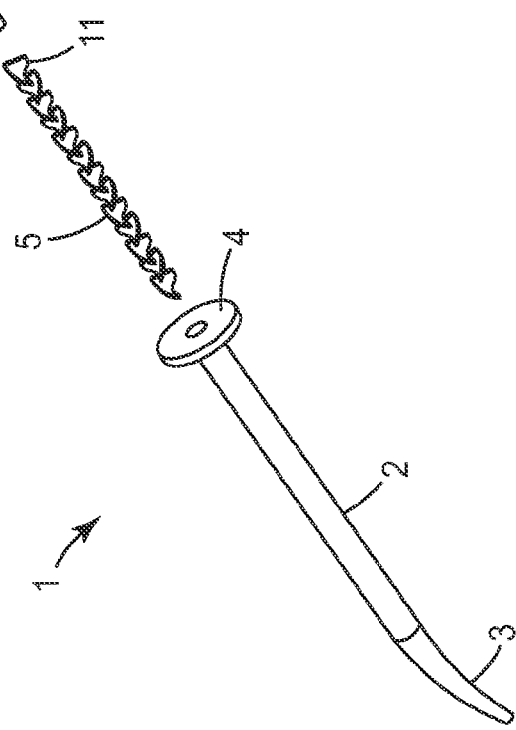

DEVICE FOR STORING, MIXING AND DISPENSING A FREE-FLOWING MATERIAL

The present application is a U.S. National Stage Application of PCT/EP 02/12899, filed 18 Nov. 2002 The application also claims the benefit under 35 U.S.C. §119 of foreign application no. DE 101 56 075.3, filed 16 Nov. 2001.

BACKGROUND OF THE INVENTION

The invention relates to a device, in particular for storing and dispensing dental materials, comprising a mixing chamber and a mixing helix inside it, which can be compressed according to requirements. The device makes it possible for the material remaining in a static mixing helix during mixing to be dispensed largely completely. Various systems for storing and mixing a multicomponent composition are known from the prior art.

SUMMARY OF THE INVENTION

Firstly there are what are known as mixing capsules, as disclosed by EP 0 157 121 A1. The components to be mixed are in this case transferred from different compartments into a mixing chamber, or sometimes they are already in the chamber, and they are mixed with the aid of a shaking device. By displacing a plunger in the capsule, the mixture is finally dispensed via a nozzle. To ensure that the mixture can be dispensed as completely as possible from the capsule, some plungers of the capsules have displacers, which can enter the nozzle, cf. DE 92 09 105 U. Said mixing capsules are suitable for mixing powders with liquids.

Double-chamber cartridges, which serve for storing a base component and a catalyst component, are also known, as described for example in EP 0 261 466 A1. For dispensing and mixing, a mixing tube in which a mixing helix is located, known as a static mixer, is fitted on these double-chamber cartridges. Static mixers of this type are known from EP 0 664 153 A1, EP 0 584 428 A1, U.S. Pat. No. 3,635,444 or U.S. Pat. No. 3,923,288. By repeated division into strands, the two components to be mixed are mixed with each other in the mixing tube as they are dispensed. The disadvantage of this device is that in every mixing operation there remains in the mixing tube a residual amount of material, which may even sometimes exceed the desired amount to be dispensed, and must be discarded unused with the static mixer as a dead volume of material. This is disadvantageous in particular where relatively expensive materials are concerned. A modification of said static mixers is disclosed in U.S. Pat. No. 6,234,795. In one specific embodiment, the mixing helix is produced from a flexible material, to allow the mixed material to be applied in a simplified way at locations which are otherwise difficult to reach.

In principle, it is an object of the present invention to provide a device which avoids the disadvantages mentioned above.

This object is achieved by a device such as that described in the claims, and a method for using the device such as that described in the claims.

The present invention provides a device which makes it possible to store different substance classes within a package and dispense them as a mixture after activation of the device, preferably to allow them to be applied directly to the desired location.

The present invention also provides a device in which relatively small amounts of free-flowing components can be stored, mixed and dispensed, it being intended that the amount of material to be discarded after use is as little as possible.

The present invention additionally provides a device which shortens the mixing of free-flowing materials, in particular the time expended from when the substances to be mixed are prepared to when the mixed material is obtained.

The following are among the advantages of the invention:

The fact that the mixing helix can be compressed in the mixing tube makes it possible to ensure that the material located in the mixing tube can be dispensed largely completely from the mixing tube. This is advantageous in particular in the case of comparatively expensive substances.

A design of the device such that the ram, cartridge and mixing tube engage in one another and are made to match one another in terms of length allows the volume of the device to be reduced to a minimum after use.

The device comprises comparatively few individual parts, depending on the embodiment preferably two to ten, preferably three to six, and as a result can be produced at relatively low cost.

The device according to this embodiment is consequently distinguished by the fact that substances or components to be stored separately of a mixture to be prepared are provided within a pack, in particular for once-only use, in a form in which they are ready for dispensing or mixing.

It is also ensured that all the substances stored in the device have the same filling date, so that incompatibilities of the substances on account of different degrading times can be ruled out.

Added to this is the fact that no disinfection is required for use of the device in the form of a once-only application.

The telescopic arrangement of the individual components, combined with the comparatively small diameter of the cartridge of the device, result in discharging forces which are favorable for handling, even in the case of relatively high paste viscosities.

The forces to be applied for activating and handling the device are usually in the range from 1 to 150 N, preferably in the range from 10 to 100 N. In the event that the mixing tube is intended or has to be emptied by means of a cartridge-application device which has an additional ram, the discharging forces may increase to approximately 2 000 N.

The terms "comprise" or "include" as used with respect to the invention introduce an enumeration of features which is not exhaustive. The term "a" is to be interpreted as an indeterminate quantitative indication meaning "at least one".

The designation "tubular element which narrows in diameter toward one end" is to be understood as meaning a substantially cylindrical hollow body with two openings, one end of which preferably tapers comparatively. If appropriate, the tubular element has in the region of this end a curvature, which preferably has a constant internal flow cross section, corresponding approximately to the outlet cross section, in order to minimize the dead volume in this region. The tubular element substantially bounds the mixing chamber and is also referred to hereafter as "mixing tube".

Further features and configurations of the invention are described in the subclaims.

The mixing helix used in the present invention usually has individual mixing elements which make it possible for the materials entering the mixing chamber to be mixed by dividing them into strands. Suitable mixing helixes of the form which can be used are described in EP 0 664 153 A1, EP 0 584 428 A1, U.S. Pat. No. 3,635,444 or U.S. Pat. No. 3,923,288. For the present invention to function, these mixing helixes must be formed however in such a way that they can be compressed according to requirements.

The term "compressible" is to be understood according to the invention as meaning that the mixing helix is designed in such a way that its axial length in particular can be reduced by exerting preferably manual pressure, but if appropriate also with the aid of additional application devices by means of a plunger. However, breaking up of the mixing helix into many small individual pieces when it is compressed, and dispensing of these individual pieces together with the mixture, should be avoided here.

The mixing helix is preferably also designed in such a way that the compressing operation takes place from the end of the mixing helix which is facing the plunger.

According to the invention, the plunger used for dispensing the mixture substantially comprises two main components, a possibly divided ram and a cartridge matching the ram.

The cartridge is suitable for separately storing at least two, if appropriate three or four, components of a mixture to be prepared. To ensure this, the cartridge possibly has at least one separating wall, which preferably runs through the axis of symmetry of the cartridge. Depending on the ratios of the substances to be mixed and the storage volumes required for them, the separating wall may, however, also be arranged off-center in the cartridge. It is also conceivable for the separating wall to have a cavity inside it. This hinders a possibly occurring permeation of substances stored in the chambers of the cartridge through the separating wall and consequently improves the storage stability.

To ensure uncomplicated functioning of the device during mixing, the viscosity of the components to be mixed or of the mixture should be adjusted appropriately for the properties of the mixing helix, in particular for its ability to be compressed.

Furthermore, it is of advantage if the ram has elements for sealing, which prevent the material to be transferred into the mixing space from escaping from the cartridge at other locations.

It is also of advantage if there are retention elements in the mixing tube and/or on the cartridge. These ensure that, when the device is activated by exerting pressure on the ram, the latter is initially moved axially forward in the cartridge, and the cartridge does not compress the mixing helix before the material has been transferred into the mixing space.

To facilitate easy handling of the device, it is also proven to be successful for it to have holding elements or finger plates, in a way comparable to a syringe, which can be attached at different locations, depending on the size of the device and its intended use. These holding elements are advantageously located in the region of the opening of the mixing tube facing the plunger and/or in the region of the opening of the cartridge facing the ram.

In particular in the case of devices which, owing to their axial length, cannot be activated with one hand in a single motion, an activation in stages or steps has proven to be advantageous. In a first step, the substances to be mixed are transferred into the mixing chamber, in that the ram is pressed into the cartridge, with the ram and cartridge being held in the customary way like a syringe. In the second step, after possibly repositioning the hand onto the finger plate located on the mixing tube, the plunger formed by the ram and cartridge is finally pressed into the mixing tube, with the device likewise being operated like a syringe.

In another embodiment, the cartridge may also be in the form of a multilumen tube.

A hard cartridge in the form of a multilumen tube is preferably used as a multichamber cartridge which can be loaded during activation when pressure is exerted in the axial direction, even without attaching holding elements.

It may also be of advantage, however, to use a flexible multilumen tube as a multicomponent cartridge, which for emptying is provided with a holding device or finger plate at its end on the ram side. The sealing beads preferably located at the ends of the ram in the case of this pair of elements to be sealed provide a seal with respect to the, in this case flexible, multicomponent cartridge.

During activation or emptying by the comparatively rigid ram, the flexible cartridge is in this case subjected only to tensile loading. If appropriate, the multilumen tube can be bent around or be provided in a bent-around form for storing and transporting purposes. This brings about a not inconsiderable reduction in length, which can be of advantage in particular when storing in a sealed-edge bag made of a composite aluminum foil.

It is likewise advantageous if the cartridge has elements for sealing (sealing elements), to prevent the substances stored in the cartridge from drying out or entering the mixing space in an uncontrolled way, and possibly reacting with one another prematurely.

These elements have bores or through-holes of any desired cross section which can be reversibly closed or opened possibly by torsion about the longitudinal axis of the cartridge (for example in the manner of a twist closure or possibly in the form of a twisted tube or a rotary slide-valve arrangement), through which the substances stored in the cartridge can be transferred into the mixing chamber when pressure is exerted on the ram.

To ensure reversible closing or opening of the cartridge in the manner of a twist closure in a reliable way, it has proven to be advantageous to provide the element or elements for sealing with a groove. This engages as a counter-bearing into one or more preferably axially parallel projections, lugs, protuberances or stages, preferably located on the inside of the mixing tube.

Alternatively, it may also be adequate to make the materials used for producing the cartridge, the element for sealing and the mixing tube match one another in such a way that retaining the desired position of the element for sealing in the mixing tube can be ensured by friction or frictional engagement.

The same effect can be ensured by making the cross sections of the mixing tube and the element for sealing match each other, for example by designing them with a triangular, square, pentagonal or hexagonal profile.

An element for sealing designed in the manner of a twist closure makes it possible to handle the device as a multidose device. After dispensing a certain amount of substance from the device, the cartridge can be closed again.

This kind of use usually comprises the following steps:

a) opening the cartridge by turning the cartridge in the mixing tube, b) partial emptying of the material stored in the cartridge into the mixing tube, c) closing the cartridge by turning the cartridge in the mixing tube, d) dispensing the material from the mixing tube by axial displacement of the ram, with the mixing helix being compressed, e) axial displacement of the ram in the opposite direction, with the compressed mixing helix substantially resuming its original shape, f) if appropriate, repetition of at least steps a) to d) until the cartridge has been substantially emptied.

To avoid closing of the mixing tube by the material to be dispensed during the multiple use described above, it is of advantage if the mixing helix extends substantially right up to the dispensing end, or the nozzle is made correspondingly short.

Depending on the embodiment of the cartridge used, the sealing elements may preferably be semicircular, short cylinder segments which are located between the mixing helix and the cartridge and seal the respective chamber with their ends on the cartridge side, are possibly formed integrally onto the mixing helix and/or onto the cartridge, possibly by the 2-component injection-molding process, or are provided separately as an individual or multiple stopper. As soon as the substances to be mixed have been transferred into the mixing chamber and the ram has been introduced into the mixing chamber, during the further dispensing operation the ram forms together with the sealing element a kind of plunger, with which the mixing helix is compressed.

This embodiment may also be modified by a sealing element which can be detached from the cartridge and by a fixed connection between the mixing tube and the cartridge in such a way that the cartridge which has contained the substances to be mixed is not or cannot be pushed forward into the mixing tube during the dispensing operation. This is of advantage in particular whenever very small amounts are preferably to be administered with the device and it is required to provide a minimum length for the device.

To ensure largely complete dispensing of the mixed substances, in the case of this embodiment the ram should substantially have axially a length which is at least or approximately as great as the length of the mixing tube and the cartridge, less the length which the compressed mixing helix takes up.

The cartridge may, however, also be sealed in some other way, for example by a comparatively thin membrane which is made to burst by excess pressure building up in the cartridge or opened, pierced or pricked by the mixing helix during activation of the device. Also conceivable is an embodiment in which the cartridge is closed by individual or multiple closing elements which are formed integrally onto the mixing helix or separate from it. The opening of the cartridge likewise takes place by an excess pressure building up in it when the ram is forced in.

To prevent unwanted activation of the device, individual components of the device are advantageously secured against being pushed into one another. Suitable securing elements comprise clasps, clips, twist closures, retention elements, threads and/or bayonet fasteners.

It is also conceivable to fit the device according to the invention, comprising the mixing tube with the collapsible mixing helix, onto customary double cartridges, as described in the introduction with reference to other documents, instead of the static mixing cannulas described there. In order that it is likewise ensured in the case of this embodiment that the mixing tube can be emptied, additional modifications to the application devices needed for double-chamber cartridges of this type are necessary in addition to paste feeders possibly opening into the mixing tube on each side. The provision of an additional ram, which is detached from the two other rams, needed for paste delivery, and is preferably located between the two cartridges, is required. When the paste delivery from the cartridge has been completed or the amount of substance desired by the user has been dispensed, the mixing cannulas can be emptied with the aid of the application device, which has a ram.

It is also conceivable furthermore to connect the device according to the invention, comprising the mixing tube with the collapsible mixing helix, to two cartridges, preferably arranged parallel to the mixing tube. An arrangement of this type consequently comprises not only the device according to the invention but also two containers for storing two substances to be mixed, which can be completely or partially emptied via openings into the mixing tube, preferably by means of plungers which are displaceable in the containers. The openings are for this purpose preferably located on the sides of the mixing tube. The mixing tube itself is emptied by means of a ram penetrating into it.

The device is suitable for the separate storing, mixing and dispensing of at least two components of a mixture to be prepared.

The mixtures to be dispensed may be: bonding agents, dental materials, such as dental impression compounds, filling materials, cements, adhesives.

The substances to be applied are usually free-flowing, possibly kneadable substances. The substances are preferably polymerizable.

Similarly, the device may be filled with all restorative and prosthetic substances common in the dental sector, such as composites, compomers, ormocers, pasty glasionomer cements, silicate cements, phosphate cements.

The components or the mixtures usually have a viscosity in the range of $0.5 \times 10^{-3}$ to $50 \times 10^3$ Pas, preferably from $1 \times 10^{-3}$ to $10 \times 10^3$ Pas.

The volume of mixture which can be applied usually lies in the range of several milliliters, for example in the range of 0.05 to 50 ml, preferably in the range of 0.2 to 20 ml.

The volume of the chambers results from the respective mixing ratio.

The volume ratio of the chambers of the cartridge lies in the range of 1:1 to 1:30, preferably in the range of 1:1 to 1:10.

The device can be produced for example by injection molding of the individual components, depending on the plastics used or their mixtures. The ram and any seals on the ram or the mixing helix and/or sealing elements and cartridges can be produced for example by a 2-component injection-molding process. The following combinations are preferred for a 2-component injection-molding process: a) mixing helix, sealing elements, cartridge, b) mixing helix, sealing elements, c) mixing helix, cartridge and/or d) sealing elements, cartridge.

Since a comparatively low-cost production process is involved here, using comparatively inexpensive raw materials, the device is suitable in particular as a once-only application unit or a single-unit dose.

Plastics which are suitable in principle for producing the device and also the multilumen tubes which can be used if appropriate as cartridges are, for example: PE, PP, PTFE, PET, PA, PBT, PVC, PVDC, EVA, PVF (polyvinyl fluoride), COC, PS, PPA, PC, LCP, POM, ABS, PEN, EVOH, PAN, PCTFE, PFA, FEP, TFF, PVDF, ETFE.

The mixing helix usually has in the range of 2 to 40 mixing elements. Suitable materials for producing the mixing helix are: thermoplastic polyether block amides (TPE-A), thermoplastic copolyesters (TPE-E), thermoplastic polyolefins (TPE-O), thermoplastic styrene copolymers (SBS), thermoplastic polyurethanes (TPU), and also thermoplastics such as PVC, PE, PUR.

The mixing helix is preferably produced from a flexible and/or brittle material and/or comprises predetermined breaking points. Mixing helixes which comprise a flexible material usually have a modulus of elasticity in the range of Shore hardness A 40 to D 80, preferably in the range of A 70 to D 60.

Depending on the substances stored in the device, the device itself is possibly packed in a blister pack.

It may be provided that the ram has a front portion and a rear portion. As a result, a space-saving arrangement of the ram in a pack can be easily achieved, in that the rear portion is for example placed parallel alongside the mixing tube or the cartridge. After unpacking, the two portions are first of all fitted together to form the ram, so that the device can be used in the accustomed way.

The ram may, however, also have further portions.

It may be provided that the portions are parts which are separate from each other.

It may then be provided that the front portion fits in the rear end of the cartridge, and that the rear portion is connected to the cartridge and/or the mixing tube by means of at least one breaking connection. This makes it possible for the rear portion to be produced together with the cartridge connected to it and/or the mixing tube connected to it, such as for example by injection molding.

It may also be provided that the rear portion is connected to the rear end of the cartridge by means of a breaking connection which is formed as a hinge and breaks while the two portions are being fitted together to form the ram or while the ram assembled from the two portions is being pressed into the cartridge. The hinge makes it easier for the two portions to be brought together when assembling the ram.

It may be provided that the portions are connected to each other at their mutually facing ends. The portions may be produced together, such as for example by injection molding.

It may be provided that the portions are connected to each other at their mutually facing ends in a pivotable manner.

It may also be provided that the portions are connected to each other by means of a film hinge.

It may be provided that the portions have corresponding coupling elements at their mutually facing ends.

It may be provided that the coupling elements permit a screw connection or a bayonet connection or a plug-in connection. For a plug-in connection, the coupling elements may for example be of a conical or wedge-shaped design.

It may also be provided that restraining means, which hinder detachment of the coupled ends, are provided at the mutually facing ends.

It may then be provided that the restraining means have latching elements. The latching elements may comprise, for example, lugs or hooks. Other restraining means are also possible, however, such as for example flutings on the faces of the ends lying against one another.

It may be provided that the front portion has a plug, which fits tightly in the rear end of the cartridge. The front portion may be designed completely or partly as a plug. To achieve the desired sealing of the cartridge chamber, the plug may consist of a softer and/or more flexible material than the rest of the portion or than the rear portion. The plug and the rest of the ram, that is the rear portion and possibly the rest of the front portion, may be produced by 2-component injection molding.

It may be provided that the rear portion has at its rear end a thumb plate with a clearance for the cartridge. This allows the rear portion to be placed right alongside the cartridge in the pack in a space-saving manner.

It may also be provided that the mixing tube has at its rear end a finger plate with a clearance for the rear portion. This allows the rear portion to be placed right alongside the mixing tube in the pack in a space-saving manner.

It may then be provided that the clearance is designed as a clamping securement. This allows the cartridge to be firmly clamped on the rear portion or the rear portion to be firmly clamped on the mixing tube.

It may be provided that the rigidity of the mixing helix varies over its length, in that for example the mixing helix is more rigid in a front region than in a rear region. As a result, a progressive force-displacement characteristic is achieved during compression, so that the mixing helix is compressed from the rear to the front.

It may be provided that the mixing helix has a greater wall thickness in a front region than in a rear region. With material properties that remain the same over the length, the rigidity of the mixing helix consequently increases from the rear to the front. Furthermore, the throughflow cross section in the mixing tube narrows from the rear to the front on account of the increasing wall thickness, which can promote the mixing effect.

It may be provided that the mixing helix is fastened at its rear end to the mixing tube and/or to the cartridge. This provides pressure relief for the mixing helix, on which a forwardly directed axial force attempting to compress the mixing helix already acts after all when the material is being dispensed from the cartridge into the mixing tube as a result of the forwardly directed material flow. Since the fastening consequently absorbs at least part of the axial force, the intrinsic rigidity of the mixing helix can be correspondingly less, which also applies to the force which has to be applied for dispensing the mixed material from the mixing tube and decreases with the intrinsic rigidity. The fastening to the mixing tube preferably takes place by means of a breaking connection, which is only broken when the dispensing of the material is completed and the cartridge is pressed into the mixing tube in order to compress the mixing helix. On the other hand, the fastening to the cartridge must be undetachable, since, when the mixing helix is compressed, its rear end of course moves forward together with the cartridge.

It may also be provided that the mixing helix is supported by its front end on the mixing tube. This allows blocking or clogging of the tapering outlet opening or nozzle of the mixing tube to be prevented, since the mixing helix then remains in the mixing tube even during compressing.

This supporting may be achieved, for example, by the mixing helix being fastened at its front end to the mixing tube.

Another example provides that the mixing tube has a stop for the front end of the mixing helix, projecting radially inward from its inner surface. The mixing helix can then support itself by its front end on this stop during compressing. The stop is preferably an annular collar or flange.

It is also possible for a ring to be formed on the front end of the mixing helix, which ring is pressed against the tapering inner surface of the mixing tube during compressing and blocks further forward movement of the mixing helix. This may also be achieved by one of the front mixing paddles of the mixing helix being made particularly thick or rigid, so that it is not deformed excessively during compressing.

The subject-matter of the present invention also includes a method for using the device, which comprises the following steps:

a) providing a device as described above, b) dispensing the components or substances stored in the cartridge into the mixing tube by exerting pressure on the ram, which can be guided in the cartridge, the mixing helix causing in said mixing tube a repeated division into strands of the components to be mixed, and c) using the ram, possibly together with the cartridge, as a plunger for dispensing the components located in the mixing tube.

BRIEF DESCRIPTION OF THE DRAWINGS

Various embodiments of the invention are described in more detail below on the basis of the accompanying drawings.

FIG. 1 is an exploded representation of a device;
FIG. 3 shows the device from FIG. 2 in the emptied state.

DETAILED DESCRIPTION OF THE PREFERRED EMBODIMENT

Figure 2:
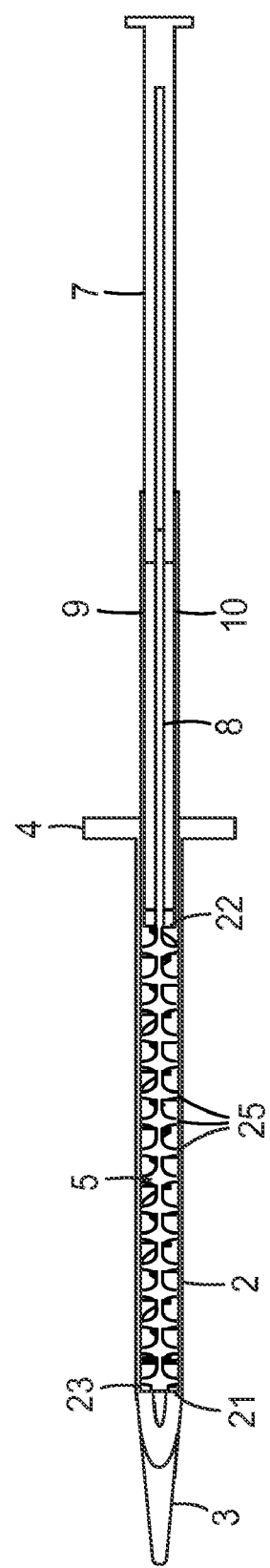
FIG. 2 is a side view of the device from FIG. 1 in the non-activated state.

FIG. 1 shows the device 1 according to the invention in an exploded representation. The device has a tubular element or mixing tube 2, which tapers toward one end or ends in a bent nozzle 3. At the other end of the mixing tube 2 there is a formed-on portion 4, for example in the form of a plate with a bore, which serves for the fixing or holding of the device during dispensing. In the mixing tube 2 there is a mixing helix 5. The mixing helix 5 can be compressed according to requirements by a plunger, which is formed by a cartridge 6 and a ram 7. The cartridge 6 has a separating wall 8, which divides the cartridge into two chambers 9 and 10. The cartridge is designed such that it is tubular and open at both ends. A ram 7, possibly divided into two or more parts, can be pushed into the cartridge 6. The ram 7 is dimensioned in such a way that it is suitable for completely dispensing the materials stored in the cartridge 6. Formed integrally onto the mixing helix 5 are closing or sealing elements 11 for closing the cartridge 6. The cartridge 6 has in the front region retention elements 12, which act in a supporting way with the effect that, on activation, the ram 7 is first pressed into the cartridge 6 before the cartridge penetrates together with the ram into the mixing tube 2.

FIG. 2 shows the device according to the invention in longitudinal section, in the non-activated form. The segmented ram 7 engages telescopically into the longitudinally divided cartridge 6, which for its part engages telescopically into the mixing tube 2.

In the device shown in side view in FIG. 3, the material located in the cartridge 6 has been dispensed by means of the ram 7 into the mixing space of the mixing tube 2 and the mixing helix 5 has been compressed by the plunger formed by the ram 7 and cartridge 6.

Figure 4:
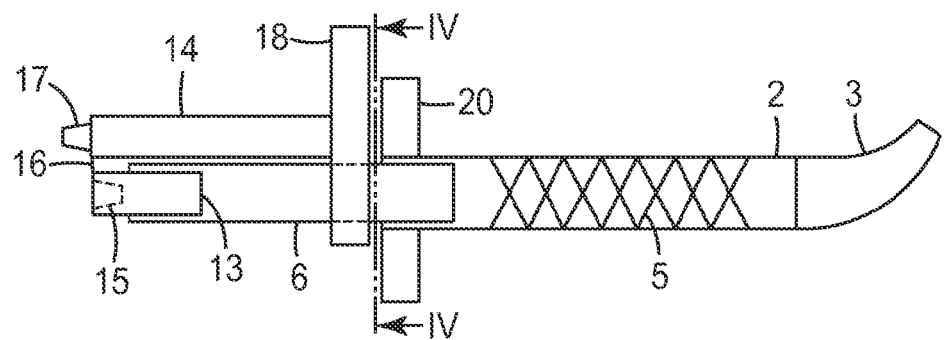
FIG. 4 is a side view of a device with a ram in a first embodiment, which is pivoted together in a space-saving manner.

FIG. 4 shows a device with a ram 7 in a first embodiment, which ram has a front portion 13 and a rear portion 14.

The front portion 13 fits with its front end (on the right in FIG. 4), which is designed as a plug and consists of a flexible material, tightly in the rear end (on the left in FIG. 4) of the cartridge 6. The rest of the front portion 13, on the other hand, is of a harder material in comparison with the plug, and the rear end (on the left in FIG. 4) of the front portion 13 protrudes from the cartridge 6 and has a conical depression 15 in its end face.

The rear portion 14 consists of the same material as the front portion 13 and is connected at its front end (on the left in FIG. 4) to the rear end of the front portion 13 in a pivotable manner by means of a film hinge 16. From the end face of this front end there protrudes a conical projection 17, the circumferential surface of which matches the circumferential surface of the conical depression 15. The depression 15 and projection 17 consequently represent corresponding coupling elements, which permit a plug-in connection between the two portions 13, 14.

Figure 5:
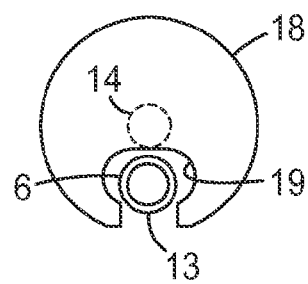
FIG. 5 is a sectional view along the line IV-IV in FIG. 4.

The rear portion 14 has at its rear end (on the right in FIG. 4) a thumb plate 18. In FIG. 5, it is clearly evident that the thumb plate 18 has at its lower edge a clearance 19, in which the cartridge 6 is accommodated when the rear portion 14 lies parallel right alongside the cartridge 6 in the space-saving position shown in FIG. 4. The opening of the clearance 19 is somewhat narrower than the outside diameter of the cartridge 6, so that the clearance 19 forms a clamping securement for the cartridge 6. Provided at the rear end of the mixing tube 2 is a finger plate 20, which may likewise have a clearance (not represented) for the rear portion 14 if the latter is to lie alongside the mixing tube 2 in the space-saving position.

Figure 6:
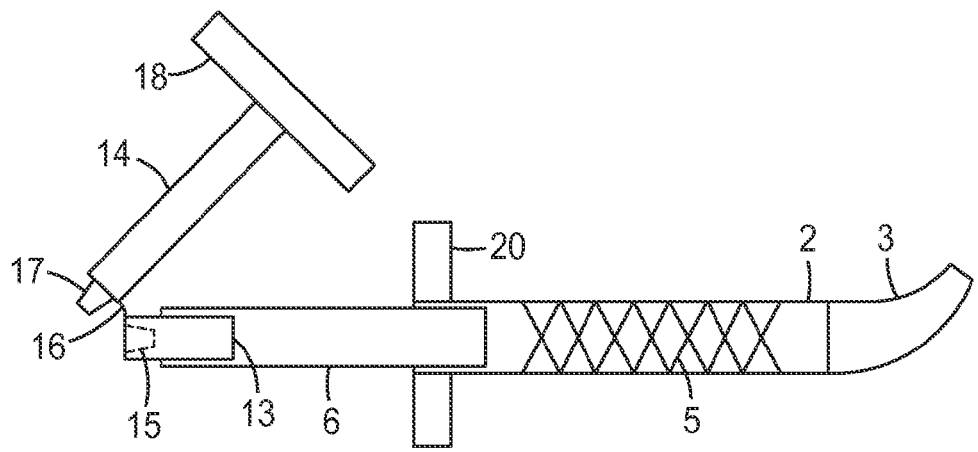
FIG. 6 shows the device from FIG. 4, the ram of which is partly pivoted open.

FIG. 6 shows the rear portion 14 in a position pivoted open by about 45°. It can easily be imagined that, because of the guidance by the film hinge 16, after a pivoting movement of altogether 180° it is coaxially in line with the front portion 13 and engages with its projection 17 in the depression 15 of the latter. The ram 7 is then assembled ready for use and can be pressed like a unitary ram into the cartridge 6, in order to dispense the materials contained in it into the mixing tube 2.

Figure 7:
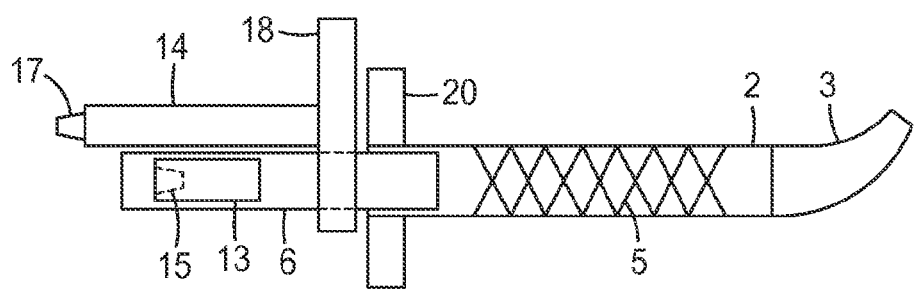
FIG. 7 is a side view of a device with a ram in a second embodiment, which lies alongside the cartridge in a space-saving manner.

FIG. 7 shows a device with a ram 7 in a second embodiment, which differs from the first embodiment of FIG. 4 in that the portions 13, 14 are parts that are separate from each other.

Here, the front portion 13 fits completely in the rear end of the cartridge 6, so that the part of the cartridge 6 lying alongside its rear end on the left serves as a guide for the front end of the rear portion 14 when the latter is pushed into the cartridge 6 when the ram 7 is assembled. This guide allows the risk of buckling to be reduced when the ram 7 is pressed into the cartridge 6.

Figure 8:
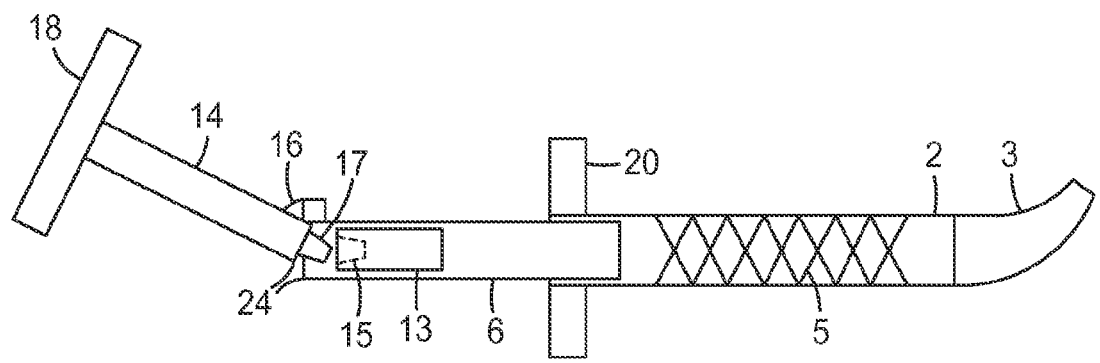
FIG. 8 is an enlarged side view of a device with a ram in a third embodiment, which is almost completely assembled.

FIG. 8 shows a device with a ram 7 in a third embodiment, which differs from the second embodiment of FIG. 7 in that the rear portion 14 is connected at its front end to the rear end of the cartridge 6 in a pivotable manner by means of a film hinge 16. The film hinge 16 is in this case broken when the rear portion 14 is pivoted out of the position shown in FIG. 8 further into the coaxially in-line position and then pressed into the cartridge 6.

If, in order to form a plug, the front portion 13 consists at least partly of a different material, for example a more flexible material, than the rear portion 14, the two portions 13, 14 may be initially produced integrally by the 2-component injection-molding process and subsequently detached from each other. This can be achieved by suitable choice of the two materials if they form a releasable connection at their interfaces when they are injection-molded onto each other. Similar effects can also be achieved by suitable choice of the injection-molding parameters or by the use of release agents. The film hinge 16 may in this case either be injection-molded from the material of the plug or from the material of the rear portion 14 and anchored with positive engagement in the other part, respectively.

If the cartridge 6 has two chambers 9, 10, and consequently the ram 7 also has two ram segments lying alongside each other (FIG. 2), the assembling of the ram 7 that is subdivided into two separate portions 13, 14 can be facilitated for example by the separating wall 8 (FIG. 2) which separates the two chambers 9, 10 from each other protruding from the rear end of the cartridge 6. This is so because the user can then initially position the two ram segments at this protruding separating wall 8, in that he places them against the two wall surfaces and then introduces them into the cartridge 6. It is also possible for the ram segments to be spread by an angle in relation to each other at their front end, thereby creating a greater degree of freedom in the positioning. In addition, the ram segments may also be connected to each other by means of releasable spacers, such as for example cross-pieces with predetermined breaking points, which break when the ram 7 is pressed into the cartridge. Furthermore, a finger plate of a flared form may be provided on the cartridge 6, so that the ram segments can be easily introduced.

LIST OF DESIGNATIONS 1 device
2 tubular element, mixing tube
3 nozzle
4 formed-on portion, holding plate
5 mixing helix optionally having a greater wall thickness in the front region than the rear region
6 cartridge
7 ram
8 separating wall
9, 10, 26 chambers
11 twist closure
12 retention elements
13 front portion
14 rear portion
15 conical depression
16 film hinge
17 coupling element permitting a screw, bayonet, plug-in, or other connection
18 thumb plate
19 clearance
21 radially inward projecting stop
22 rear end of mixing helix fastened to the mixing tube and/or to the cartridge.
23 front end of mixing helix fastened to the mixing tube
24 restraining means comprising latching elements
25 predetermined breaking points of the mixing helix

The invention claimed is:

1. A device for storing, mixing, and dispensing at least one material comprising:
a mixing tube having an end; a mixing helix located in said tube, the mixing helix constructed to mix the at least one material and to be compressed within the mixing tube; and
a plunger located in the mixing tube, the plunger comprising:
a cartridge for storing the at least one material and a ram located in the cartridge wherein the device is constructed such that the ram dispenses the at least one material stored in the cartridge into the mixing tube, the mixing helix mixes the at least one material, and the plunger subsequently compresses the mixing helix while dispensing the mixed material from the end of the mixing tube.

2. The device of claim 1, wherein the cartridge is arranged laterally offset with respect to the mixing tube and from which the material to be mixed can be transferred into the mixing tube.

3. The device of claim 1, wherein the mixing helix is adapted to mix the materials by dividing the materials into strands as the materials pass through the elements of the mixing helix.

4. The device of claim 3, the mixing helix comprising 2 to 40 strand-dividing sections.

5. The device of claim 1, the mixing helix comprises a flexible material or has predetermined breaking points or has predetermined buckling points.

6. The device of claim 1, the cartridge comprising at least two chambers.

7. The device of claim 1, the cartridge comprising at least one separating wall.

8. The device of claim 1, further comprising at least one holding element for handling the device.

9. The device of claim 1, wherein the a volume of the mixed material is from 0.05 ml to 50 ml.

10. The device of claim 1, the cartridge further comprising free-flowing components of the at least one material stored therein.

11. The device of claim 10, wherein the components have a viscosity in the range of $0.5 \times 10^{-3}$ to $50 \times 10^3$ Pas.

12. The device of claim 10, wherein the components to be mixed are constituents of dental materials.

13. The device of claim 1, wherein the ram has a front portion and a rear portion, and further wherein the cartridge comprises a rear end.

14. The device of claim 13, wherein the front portion of the ram fits in the rear end of the cartridge, and further the rear portion of the ram is connected to the cartridge by at least one breakable connection.

15. The device of claim 14, wherein the at least one breakable connection is formed as a hinge and breaks while the front portion and rear portion are fitted together to form the ram, or while the ram that is assembled from the two portions is pressed into the cartridge.

16. The device of claim 13, wherein the front portion and the rear portion being pivotally connected.

17. The device of claim 16, wherein the front portion and the rear portion are connected by a film hinge.

18. The device of claim 13, wherein the front portion and the rear portion have corresponding coupling elements.

19. The device of claim 13 wherein the front portion fits tightly in the rear end of the cartridge.

20. The device of claim 13, wherein the rear portion comprises a rear end, the rear portion further comprises at its rear end a thumb plate with a clearance for the cartridge.

21. The device of claim 13 comprises a rear end, and further wherein the mixing tube comprises at its rear end a finger plate.

22. The device of claim 20, said thumb plate having a clearance that allows the cartridge to be firmly clamped on the rear portion, or the rear portion to be firmly clamped on the mixing tube.

23. The device of claim 1, wherein the mixing helix comprises a front region and a rear region, and further the mixing helix is more rigid in the front region than in the rear region.

24. The device of claim 23, the mixing helix further having a greater wall thickness in the front region than in the rear region.

25. The device of claim 1, wherein the mixing helix comprises a rear end, and further the mixing helix is fastened at its rear end to the mixing tube and/or to the cartridge.

26. The device of claim 1, wherein the mixing helix comprises a front end, and further the mixing helix is supported by its front end on the mixing tube.

27. The device of claim 26, the mixing helix being fastened at its front end to the mixing tube.

28. The device of claim 26, the mixing tube further comprises a stop, projecting radially inward from its inner surface.

* * * * *

UNITED STATES PATENT AND TRADEMARK OFFICE
CERTIFICATE OF CORRECTION

| | | |
|---|---|---|
| PATENT NO. | : 7,806,297 B2 | |
| APPLICATION NO. | : 10/495324 | |
| DATED | : October 5, 2010 | |
| INVENTOR(S) | : Helmut Pauser | |

It is certified that error appears in the above-identified patent and that said Letters Patent is hereby corrected as shown below:

<u>Column 11</u>

Line 43; Below "19 clearance" insert -- 20 finger plate --.

<u>Column 12</u>

Line 20; Claim 9, delete "the a" and insert -- a --, therefor.
Line 52; Claim 21, before "comprises" insert -- wherein the mixing tube --.
Line 53; Claim 21, before "comprises" delete "wherein the mixing tube".

<u>Column 14</u>

Line 2; Claim 28, before "projecting" delete ",".

Signed and Sealed this
Twenty-ninth Day of November, 2011

David J. Kappos
*Director of the United States Patent and Trademark Office*